(12) United States Patent
Lee et al.

(10) Patent No.: US 9,772,561 B2
(45) Date of Patent: Sep. 26, 2017

(54) SEMICONDUCTOR MANUFACTURING METHOD AND TOOL

(71) Applicant: Taiwan Semiconductor Manufacturing Company, Ltd., Hsin-Chu (TW)

(72) Inventors: Yung-Yao Lee, Zhubei (TW); Heng-Hsin Liu, New Taipei (TW); Yi-Ping Hsieh, Hsinchu (TW); Ying Ying Wang, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 176 days.

(21) Appl. No.: 14/804,186

(22) Filed: Jul. 20, 2015

(65) Prior Publication Data
US 2016/0240443 A1 Aug. 18, 2016

Related U.S. Application Data

(60) Provisional application No. 62/116,117, filed on Feb. 13, 2015.

(51) Int. Cl.
| | | |
|---|---|---|
| *G03F 9/00* | (2006.01) | |
| *G03F 7/20* | (2006.01) | |
| *H01L 21/66* | (2006.01) | |
| *G06F 17/50* | (2006.01) | |
| *G01N 21/95* | (2006.01) | |

(52) U.S. Cl.
CPC ........ *G03F 7/70633* (2013.01); *G03F 9/7003* (2013.01); *G06F 17/5081* (2013.01); *H01L 22/20* (2013.01); *G01N 21/9501* (2013.01); *H01L 22/12* (2013.01)

(58) Field of Classification Search
CPC ... G03F 7/70633; G03F 9/7003; H01L 22/20; G06F 17/5081
USPC ..................................................... 430/22, 30
See application file for complete search history.

(56) References Cited

U.S. PATENT DOCUMENTS

| | | |
|---|---|---|
| 8,703,368 B2 | 4/2014 | Lee et al. |
| 9,613,002 B2 | 4/2017 | Han et al. |
| 2008/0174753 A1 | 7/2008 | Mos et al. |

FOREIGN PATENT DOCUMENTS

| | | |
|---|---|---|
| KR | 20080069136 A | 7/2008 |
| TW | 201432831 A | 8/2014 |

OTHER PUBLICATIONS

Huang et al., "Using Intra-Field High Order Correction to Achieve Overlay Requirement beyond Sub-40nm Node," Proc. of SPIE, vol. 7272, Mar. 23, 2009, 9 pgs.

*Primary Examiner* — Christopher Young
(74) *Attorney, Agent, or Firm* — Slater Matsil, LLP

(57) ABSTRACT

An overlay measurement and correction method and device is provided. In an embodiment the measurement device takes measurements of a first semiconductor wafer and uses the measurements in a plurality of correction techniques to generate an overlay correction model. The plurality of correction techniques include a first order correction, a first intra-field high order parameter correction and a first inter-field high order parameter correction. The model is used to adjust the exposure parameters for the exposure of the next semiconductor wafer. The process is repeated on each semiconductor wafer for a run-to-run analysis.

20 Claims, 8 Drawing Sheets

SEMICONDUCTOR MANUFACTURING METHOD AND TOOL

This application claims priority to U.S. Provisional Patent Application No. 62/116,117 filed Feb. 13, 2015, and entitled "Semiconductor Manufacturing Method and Tool," which application is incorporated herein by reference.

BACKGROUND

Generally, active devices and passive devices are formed on and in a semiconductor substrate. Once formed, these active devices and passive devices may be connected to each other and to external devices using a series of conductive and insulative layers. These layers may help to interconnect the various active devices and passive devices as well as provide an electrical connection to external devices through, for example, a contact pad.

To form these interconnections within these layers, a series of photolithographic, etching, deposition, and planarization techniques may be employed. However, the use of such techniques has become more complicated as the size of active and passive devices have been reduced, causing a reduction in the size of the interconnects to be desired as well. As such, improvements in the formation and structure of the interconnects are desired in order to make the overall devices smaller, cheaper, and more efficient with fewer defects or problems.

BRIEF DESCRIPTION OF THE DRAWINGS

Embodiments of the present disclosure are best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

DETAILED DESCRIPTION

In the following description, specific details are set forth to provide a thorough understanding of embodiments of the present disclosure. However, one having ordinary skill in the art will recognize that embodiments of the disclosure can be practiced without these specific details. In some instances, well-known structures and processes are not described in detail to avoid unnecessarily obscuring embodiments of the present disclosure.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are intended for illustration.

Figure 1:
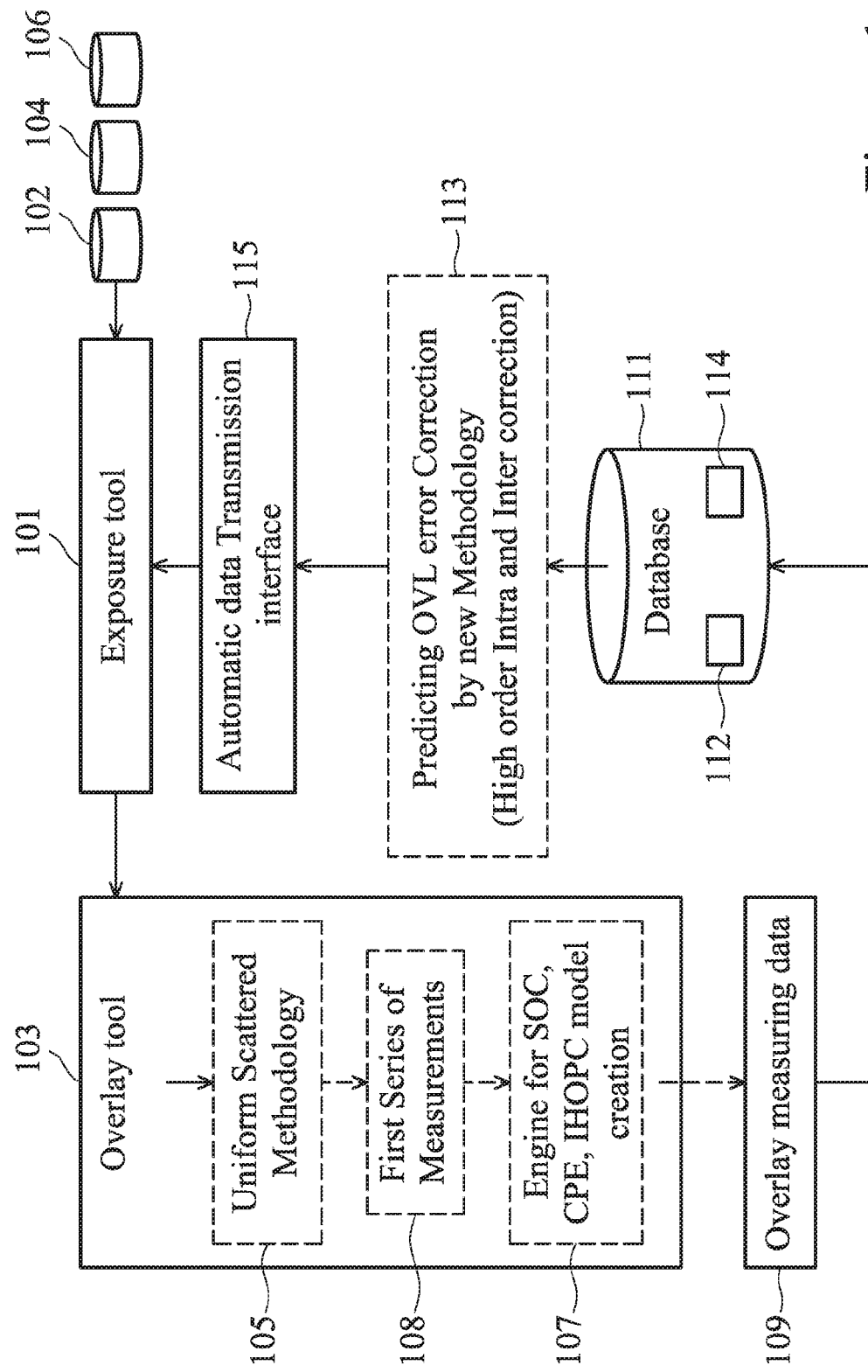
FIG. 1 illustrates a process flow diagram for a uniform scattered methodology for overlay correction according to one or more embodiments of the present disclosure.

With reference now to FIG. 1, there is illustrated a process flow in accordance with an embodiment that may be used to measure and compensate for overlay misalignments that occur during the manufacturing of a first semiconductor wafer 102 and a second semiconductor wafer 104 that each comprise, e.g., semiconductor devices. In particular, semiconductor devices, such as semiconductor dies, microelectromechanical (MEM) devices, image sensors, or the like, that may be manufactured using semiconductor manufacturing processes such as photolithographic masking and etching, annealing, implantation, or the like, may have minute variations caused by the processing of different wafers. For example, run-to-run (R2R) variations may be measured in order to try and compensate for these variations between individual runs.

However, the more measurements that are taken on each of the wafers (e.g., the first semiconductor wafer 102 and the second semiconductor wafer 104), the less efficient the overall process becomes, as each measurement point takes time and energy to take, analyze, and then, ultimately, adjust in order to help the next semiconductor wafer to be manufactured. As such, there is a constant tension between the number of measurements that should be taken and the efficiency of the overall process to form the semiconductor devices in a cost-effective time.

FIG. 1 illustrates one such process that may be utilized to provide an efficient process to measure and compensate for overlay variations. While illustrated in FIG. 1 as a circular process, the first semiconductor wafer 102 may enter the process by initially placing a layer that is susceptible to overlay misalignment, such as a layer of photolithographic material 203 (not illustrated in FIG. 1 but illustrated and described below with respect to FIG. 2) onto the first semiconductor wafer 102.

Figure 2:
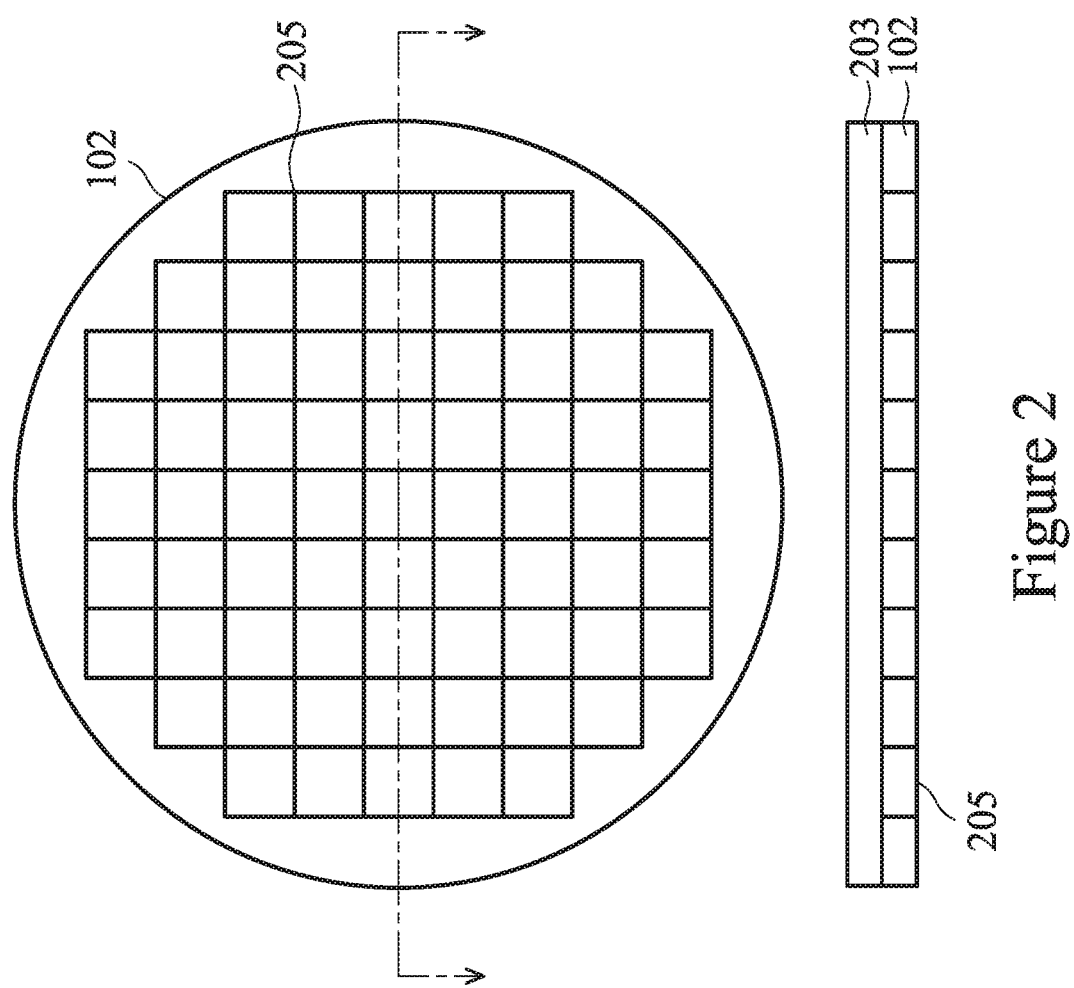
FIG. 2 illustrates a top down and cross-sectional view of a semiconductor wafer according to one or more embodiments of the present disclosure.

Looking at FIG. 2, FIG. 2 illustrates the first semiconductor wafer 102 and the photolithographic material 203 that is susceptible to undesirable overlay variations. The first semiconductor wafer 102 may comprise multiple structures (not separately illustrated in FIG. 2) that may be used to form, e.g., semiconductor dies 205 or other semiconductor devices. In an embodiment the first semiconductor wafer 102 may comprise, e.g., a first substrate, a first active device layer, and first metallization layers. In an embodiment the first substrate may comprise bulk silicon, doped or undoped, or an active layer of a silicon-on-insulator (SOI) substrate. Generally, an SOI substrate comprises a layer of a semiconductor material such as silicon, germanium, silicon germanium, SOI, silicon germanium on insulator (SGOI), or combinations thereof. Other substrates that may be used include multi-layered substrates, gradient substrates, or hybrid orientation substrates.

The first active device layer may comprise a wide variety of active devices such as transistors and the like and passive devices such as capacitors, resistors, inductors and the like that may be used to generate the desired structural and functional parts of the design for the first semiconductor wafer 102. The active devices and passive devices within the first active device layer may be formed using any suitable methods either within or else on the first substrate.

The first metallization layers are formed over the first substrate and the first active device layer and are designed to connect the various active devices to form functional circuitry for the first semiconductor wafer 102. In an embodiment the first metallization layers are formed of alternating layers of dielectric and conductive material and may be formed through any suitable process (such as deposition, damascene, dual damascene, etc.). In an embodiment there may be four layers of metallization separated from the first substrate by at least one interlayer dielectric layer (ILD), but the precise number of metallization layers is dependent upon the design of the first semiconductor wafer 102.

In an embodiment the photolithographic material 203 is a photosensitive composition that may be used, along with another process such as an etching process or a plating process, in order to pattern the underlying layers (e.g., the first metallization layers) into the desired shapes. As such, while illustrated in FIG. 2 as being located over the first semiconductor wafer 102 as a whole (including over the first substrate, the first active device layer, and the first metallization layers), the photolithographic material 203 may be coated or formed over any of the layers. In other words, the photolithographic material 203 may be formed and placed at any desired point during the manufacturing process of the devices from the first semiconductor wafer 102.

The photolithographic material 203 may be used to help translate a patterned energy source into a physical mask which may then be used to help pattern an underlying physical layer. In an embodiment the photolithographic material 203 comprises a polymer resin which, when reacted with an acid, will change a physical property such as its solubility in those portions of the photolithographic material 203 exposed to light. The photolithographic material 203 may additionally include an acid generator, such as a photoacid generator, that will absorb the patterned energy in those portions of the photolithographic material 203 that are exposed in order to generate the acid for the reaction with the polymer resin. The photolithographic material 203 may be applied using a solvent, and a pre-exposure bake may then be performed in order to drive off the solvent and leave the polymer resin, the photoacid generator, and any desired additives (e.g. a cross-linking additive), on the first semiconductor wafer 102.

Returning now to FIG. 1, once the photolithographic material 203 has been placed, the photolithographic material 203, along with the first semiconductor wafer 102, is placed within an exposure tool 101. In an embodiment the exposure tool 101 comprises an imaging device (not separately illustrated). The imaging device may comprise a support plate, an energy source, a patterned mask between the support plate and the energy source, and optics. In an embodiment the support plate is a surface to which the first semiconductor wafer 102 and the photolithographic material 203 may be placed or attached and which provides support and control to the first semiconductor wafer 102 and the photolithographic material 203 during exposure of the photolithographic material 203. Additionally, the support plate may be movable along one or more axes, as well as providing any desired heating or cooling to the first semiconductor wafer 102 and the photolithographic material 203 in order to prevent temperature gradients from affecting the exposure process.

In an embodiment the energy source supplies energy such as light to the photolithographic material 203 in order to induce a reaction of the photoacid generators, which in turn reacts with the polymer resin to chemically alter those portions of the photolithographic material 203 to which the energy impinges. In an embodiment the energy may be electromagnetic radiation, such as g-rays (with a wavelength of about 436 nm), i-rays (with a wavelength of about 365 nm), ultraviolet radiation, far ultraviolet radiation, x-rays, electron beams, or the like. The energy source may be a source of the electromagnetic radiation, and may be a KrF excimer laser light (with a wavelength of 248 nm), an ArF excimer laser light (with a wavelength of 193 nm), a F2 excimer laser light (with a wavelength of 157 nm), or the like, although any other suitable source of energy, such as mercury vapor lamps, xenon lamps, carbon arc lamps or the like, may alternatively be utilized.

The patterned mask is located between the energy source and the photolithographic material 203 in order to block portions of the energy to form a patterned energy prior to the energy actually impinging upon the photolithographic material 203. In an embodiment the patterned mask may comprise a series of layers (e.g., substrate, absorbance layers, anti-reflective coating layers, shielding layers, etc.) to reflect, absorb, or otherwise block portions of the energy from reaching those portions of the photolithographic material 203 which are not desired to be illuminated. The desired pattern may be formed in the patterned mask by forming openings through the patterned mask in the desired shape of illumination.

Optics may be used to concentrate, expand, reflect, or otherwise control the energy as it leaves the energy source, is patterned by the patterned mask, and is directed towards the photolithographic material 203. In an embodiment the optics comprise one or more lenses, mirrors, filters, combinations of these, or the like to control the energy along its path. Additionally, elements of the optics (e.g., individual lenses, mirrors, etc.) may also be located at any location between the energy source (where the energy is generated) and the photolithographic material 203.

In an embodiment the first semiconductor wafer 102 and the photolithographic material 203 are placed on the support plate. Once the pattern has been aligned to the first semiconductor wafer 102, the energy source generates the desired energy (e.g., light) which passes through the patterned mask and the optics on its way to the photolithographic material 203. The patterned energy impinging upon portions of the photolithographic material 203 induces a reaction of the photoacid generators within the photolithographic material 203. The chemical reaction products of the photoacid generators absorption of the patterned energy (e.g., acids) then reacts with the polymer resin, chemically altering the photolithographic material 203 in those portions that were illuminated through the patterned mask.

In an embodiment the imaging device will expose only a first portion of the photolithographic material 203 over the first semiconductor wafer 102. This first portion is called a field, and can generally correspond to the location of, e.g., a single one of the semiconductor dies 205. Once the photolithographic material 203 within the field has been exposed, the imaging device will "step" to an adjacent section of the photolithographic material 203 (e.g., over a second one of the semiconductor dies 205) and expose a second portion of the photolithographic material 203. This process will continue in a step-by-step fashion to expose a field over each one of the semiconductor dies 205 until all of the photolithographic material 203 has been exposed as desired.

Once the photolithographic material 203 has been exposed, the photolithographic material 203 may be developed. In an embodiment a developer (not separately illustrated) may be placed in contact with the exposed and unexposed portions of the photolithographic material 203. The difference in properties caused by the exposure is utilized to separate the exposed region from the non-exposed region, thereby forming a patterned photoresist on the first semiconductor wafer 102.

However, as semiconductor devices shrink in size, misalignments that can occur even without error from wafer to wafer can significantly affect the alignment. Further, as process windows are reduced along with the size of the devices, tolerances for misalignments are also reduced, as even small misalignments can result in defective devices being manufactured.

As such, after the photolithographic material 203 has been exposed in the exposure tool 101 and developed, the first semiconductor wafer 102 and the photolithographic material 203 are sent to an overlay tool 103 so that a first series of measurements 108 can be taken to measure the amount of undesired misalignment that has occurred during the exposure process. In an embodiment the overlay tool 103 may utilize an image based overlay metrology system or a diffraction-based overlay metrology system. For example, the overlay tool 103 may comprise a camera in order to take one or more images of the photolithographic material 203 after development. The images generally include an image of one or more alignment marks (not separately illustrated) that have been formed on the first semiconductor wafer 102, and the alignment marks and their relative position to the photolithographic material 203 on the image are then analyzed in order to determine overlay measuring data 109.

However, the number of measurements which are taken is in constant tension with the speed of the process. In particular, the greater the number of measurements that are taken and analyzed, the more detailed the overlay measuring data 109 can be, and the greater the correction that can be provided. However, the greater the number of measurements, the longer the measurement and analysis will be, and the less efficient the measurement and analysis process will be in terms of time and money.

As such, to reduce the number of measurements that are utilized to analyze the first semiconductor wafer 102, the overlay tool 103 will utilize a uniform scattered methodology 105 to measure the overlay error of the first semiconductor wafer 102. By using such a method as the uniform scattered methodology 105, the overall number of measurements may be reduced while still maintaining an overlay correction that reduces the defects caused by overlay issues. Additionally, by using the process described further below in conjunction with the uniform scattered methodology 105, the overlay correction will actually be enhanced, even with the reduced number of measurements.

Figure 3:
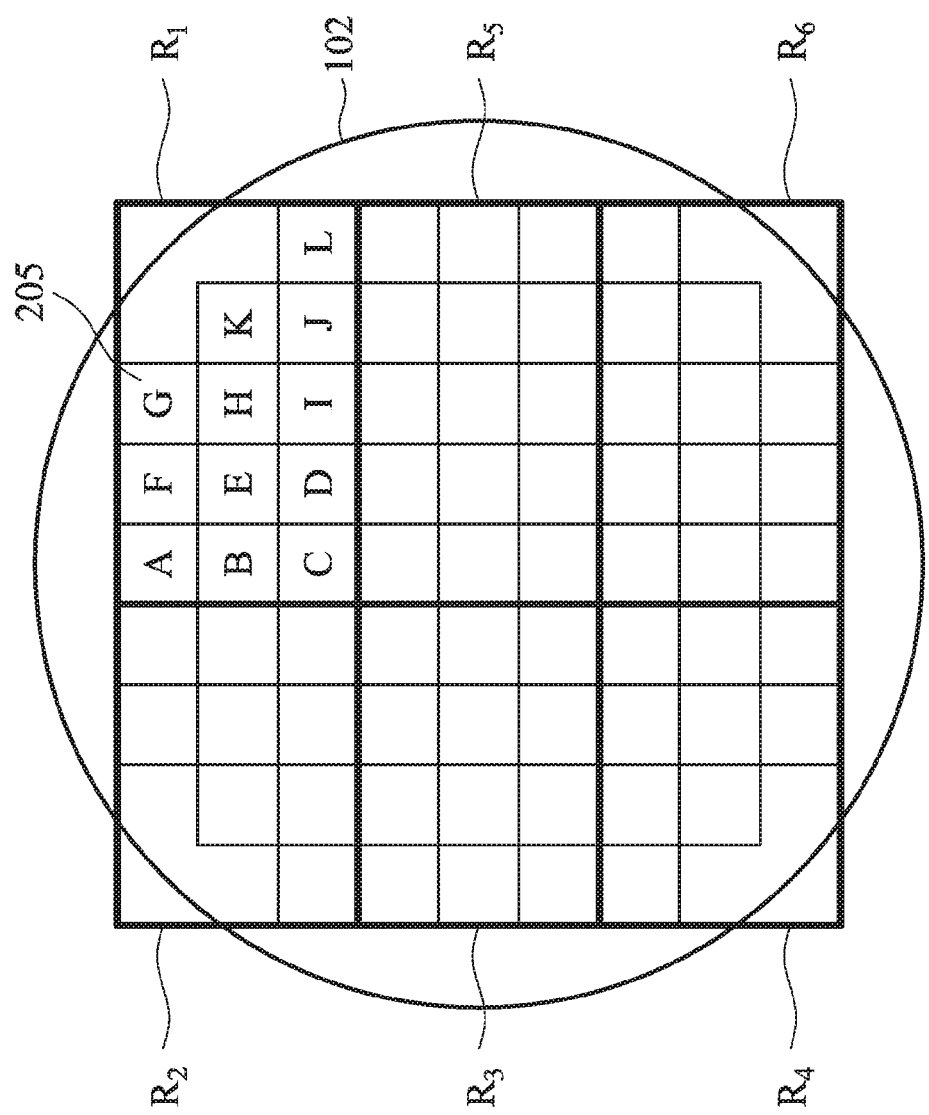
FIG. 3 illustrates a division of the semiconductor wafer into separate regions according to an embodiment of the present disclosure.

FIG. 3 illustrates a first step in the uniform scattered methodology 105 measurement process. In an embodiment the first semiconductor wafer 102 is first separated into separate regions, such as a first region $R_1$, a second region $R_2$, a third region $R_3$, a fourth region $R_4$, a fifth region $R_5$, and a sixth region $R_6$. In an embodiment the first region $R_1$, the second region $R_2$, the third region $R_3$, the fourth region $R_4$, the fifth region $R_5$, and the sixth region $R_6$ may be based upon the individual number of semiconductor dies 205 or exposure fields that are located on the first semiconductor wafer 102. For example, the separate regions may be separated such that each has three semiconductors die 205 in a vertical direction, and a relatively equal (although one may have more than the other) number of semiconductor dies 205 in a horizontal direction.

However, while the above description utilizes a relatively equal number of semiconductor dies 205, this is intended to be illustrative and is not intended to limit the embodiments. Rather, any suitable separation of the first semiconductor wafer 102 into discrete regions, such as the first region $R_1$, the second region $R_2$, the third region $R_3$, the fourth region $R_4$, the fifth region $R_5$, and the sixth region $R_6$ may alternatively be utilized, and all such separations are fully intended to be included within the embodiments. For example, the first semiconductor wafer 102 may be divided into the separate regions based on mask label counts, wherein all of the different regions compose to the full first semiconductor wafer 102.

Once the semiconductor wafer 102 has been separated into the first region $R_1$, the second region $R_2$, the third region $R_3$, the fourth region $R_4$, the fifth region $R_5$, and the sixth region $R_6$, measurements may be taken from each of the semiconductor dies 205 within each region. In an embodiment the overlay tool 103 may perform a measurement of each semiconductor die 205 within, e.g., the first region $R_1$. For example an image may be taken and analyzed by the camera of one or more measurement sites 403 on each of the semiconductor dies 205 (e.g., semiconductor dies labeled "A", "B", "C", "D", etc.).

Figure 4:
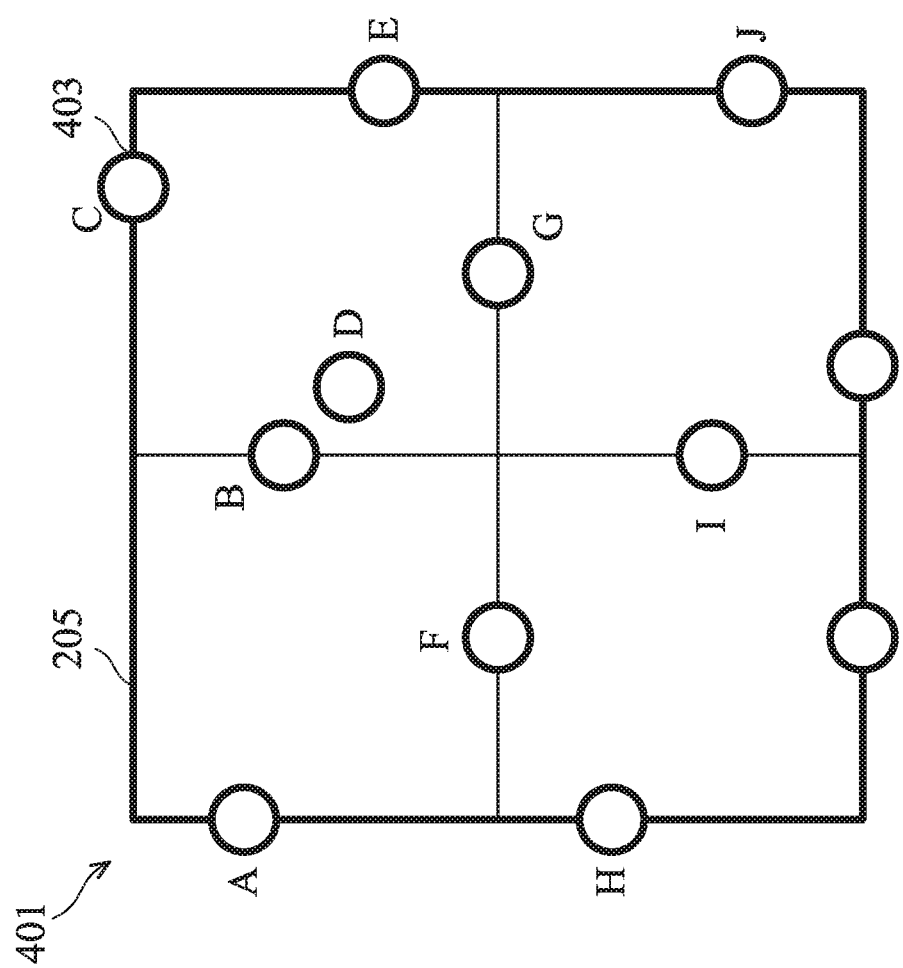
FIG. 4 illustrates a measurement map that may be used to determined measurement location according to an embodiment of the present disclosure.

FIG. 4 illustrates a measurement map 401 which may be based upon alignment marks formed within the semiconductor dies 205 on the first semiconductor wafer 102. In an embodiment the measurement map 401 may comprise one or more measurement sites 403, such as twelve points (ten of which are labeled "A"-"J" and two of which are unlabeled) 403 where an alignment mark may be located within the individual semiconductor dies 205 or fields. These measurement sites 403 may be utilized to provide the overlay tool 103 the location of specific points of measurement to be taken. However, any suitable number of measurement sites 403 may alternatively be utilized.

Returning to FIG. 3, in order to make a measurement for each of the individual semiconductor dies 205, the overlay tool 103 utilizes a reduced number of points to take a measurement from each one of the semiconductor dies 205. For example, for the semiconductor die 205 labeled "A" in FIG. 3, the overlay tool 103 will make a single measurement using a randomly selected one of the measurement sites 403 provided by the measurement map 401. For the semiconductor die 205 labeled "B" the overlay tool 103 will also take a random single measurement, although it may or may not be the same measurement location on the measurement map 401 as the semiconductor die 205 labeled "A."

In an example the overlay tool 103 may take a measurement by first determining which one of the measurement sites 403 to measure. For example, the overlay tool 103 will randomly select one of the twelve measurements sites 403 (such as site "D") within the measurement map 401. Once the measurement site 403 site has been chosen, the overlay tool 103 will then take an image of that measurement site 403 using, e.g., the imaging camera. Once the image has been taken, the overlay tool 103 will compare the image of the alignment mark with a reference to determine an alignment overlay error for the measurement site 403 in the semiconductor die 205.

This process is repeated until each of the semiconductor dies 205 within the first region $R_1$ has a measurement taken from a location within each of the semiconductor dies 205. In an embodiment, a random one of the measurement sites 403 is chosen from the measurement map 401, an image of that measurement site 403 is taken, and an overlay error is determined. As such, in the embodiment illustrated in FIG. 3 wherein the first region $R_1$ comprises twelve semiconductor dies 205, twelve measurements are taken, with one measurement being taken from each semiconductor die 205 within the first region $R_1$.

In an embodiment, similar measurement processes are performed within the remaining regions, such as the second region $R_2$, the third region $R_3$, the fourth region $R_4$, the fifth region $R_5$, and the sixth region $R_6$. For example, for each region, at least one measurement site 403 is randomly (based on the measurement map 401) measured within each semiconductor die 205 within the individual region. This is repeated until all of the semiconductor dies within each region have had at least one measurement taken.

Additionally, if desired, sampling may be reduced even further by identifying separate regions, such as the second region $R_2$, the third region $R_3$, the fourth region $R_4$, the fifth region $R_5$, and the sixth region $R_6$, that may have similar overlay errors. For example, if two models (e.g., an inter-field x-direction translation ($T_x$), and inter-field y-direction translation ($T_y$), a wafer rotation ($R_w$), a non-orthogonality (N), an x-direction wafer scaling coefficient ($S_x$), a y-direction wafer scaling coefficient ($S_y$)), a symmetrical field rotation (Rs), an asymmetrical field rotation ($R_A$), a symmetrical field magnification ($M_s$), or an asymmetrical field magnification ($M_A$), may be identified as being similar.

For example, if the difference in the inter-field x-direction translation $T_x$ is less than about 30 nm (e.g., |Tx−Tx'|<30 nm) then the regions may be said to be similar. Additionally, or alternatively, if the difference in the inter-field y-direction translation $T_y$ is less than about 30 nm (e.g., |Ty−Ty'|<30 nm), if the difference in the wafer rotation $R_w$ is less than about 1 urd (e.g., |Rw−Rw'|<1 urd), if the difference in the non-orthogonality N is less than about 1 urd (e.g., |N−N'|<1 urd), if the difference in the x-direction wafer scaling coefficient $S_x$ is less than about 1 ppm (e.g., |Sx−Sx'|<1 ppm, wherein a ppm is 1/1000000 meter)), if the difference in the y-direction wafer scaling coefficient $S_y$ is less than about 1 ppm (e.g., |Sy−Sy'|<1 ppm), if the difference in the symmetrical field magnification $M_s$ is less than 1 ppm (e.g., |Ms−Ms'|<1 ppm), if the difference in the asymmetrical field magnification $M_A$ is less than about 1 ppm (e.g., |Ma−Ma'|<1 ppm), if the difference in the symmetrical field rotation $R_s$ is less than about 1 urd (e.g., |Rs−Rs'|<1 urd), or if the difference in the asymmetrical first field rotation $R_A$ is less than 1 urd (e.g., |Ra−Ra'|<1 urd), then two separate regions may be said to be similar.

By identifying the different regions that may have similar overlay errors, even further reductions in the number of measurements may be achieved. In particular, once different regions have been identified as being similar, then a single measurement may be taken from one or the other of the regions (e.g., the second region $R_2$) and then the same measurement may be used for the other region (e.g., the third region $R_3$) which is similar. As such, even fewer measurements may be taken, resulting in even further efficiencies in time and cost.

Figure 5:
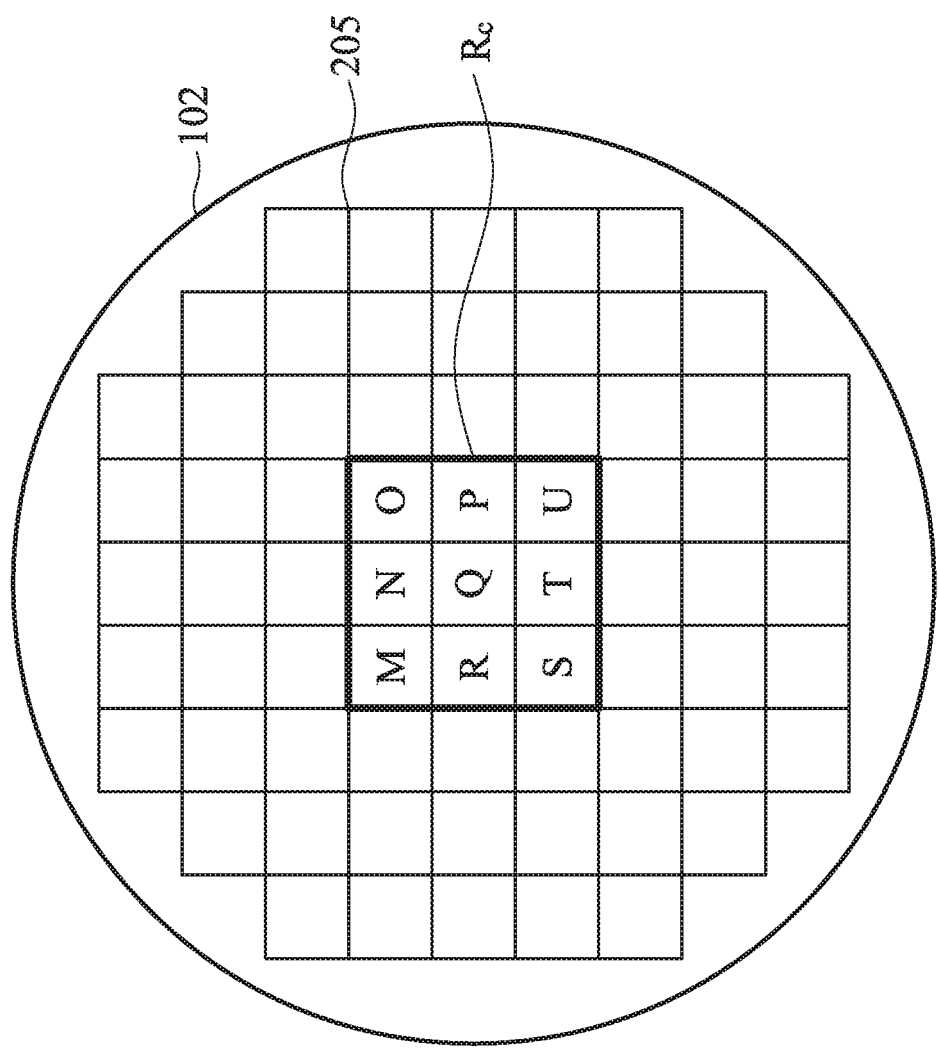
FIG. 5 illustrates a central region of the semiconductor wafer according to one or more embodiments of the present disclosure.

FIG. 5 illustrates a next step in the uniform scattering methodology 105. In an embodiment the next step comprises taking a series of measurements in a central region $R_c$ of the first semiconductor wafer 102 for use in a higher order correction technique (described further below). In an embodiment the central region $R_c$ may be chosen to be a square of nine of the semiconductor die 205 centered within the first semiconductor wafer 102. However, any suitable number of semiconductor dies 205, such as a number of two or greater die, may be included within the central region $R_c$ of the first semiconductor wafer 102.

Once the semiconductor dies 205 within the central region $R_c$ are identified, each one of the semiconductor dies 205 within the central region $R_c$ are again measured. In an embodiment the semiconductor dies 205 within the central region $R_c$ are measured in a similar fashion as the semiconductor dies 205 within the first region $R_1$. For example, the overlay tool 103 randomly chooses a measurement site 403 from the measurement map 401 and, for each semiconductor die 205, takes an image and compares that image to a reference to determine the overlay error at each measurement site 403. However, also similar to the measurement of the semiconductor dies 205 in the first region $R_1$, a single measurement is taken within each semiconductor die 205 in the central region $R_c$. As such, in the embodiment illustrated in FIG. 5 in which the central region $R_c$ comprises nine semiconductor dies 205, nine measurements are taken.

Returning now to FIG. 1, once the overlay tool 103 has performed the uniform scattered methodology 105, the first series of measurements 108 are then forwarded to a model creation engine 107. The model creation engine 107 may be a program or set of instructions stored on a non-transitory medium that are run on, e.g., a a processing system (not separately illustrated in FIG. 1). The processing system may be a computer platform that may be used to implement any or all of the processes discussed herein, and may comprise a central processing unit (CPU), memory, and a mass storage device. The CPU may comprise any type of electronic data processor, and the memory may comprise any type of system memory, such as static random access memory (SRAM), dynamic random access memory (DRAM), or read-only memory (ROM).

In an embodiment the model creation engine 107 receives the first series of measurements 108 taken (e.g., the measurements of the overlay errors) and generates one or more overlay error models that describe the various errors for the first semiconductor wafer 102 as a whole and which may be used to compensate for the overlay errors in the next semiconductor wafer to be exposed (e.g., the second semiconductor wafer 104). In a particular embodiment the model creation engine 107 takes the first series of measurements 108 and performs a first order correction on it, wherein variations are assumed to vary linearly across the first semiconductor wafer 102. For example, the model creation engine 107 may perform a smart overlay control (SOC) in which the incoming first series of measurements 108 (e.g., the measurements from each of the semiconductor dies 205 on the first semiconductor wafer 102) are placed into an overlay control table (not separately illustrated in FIG. 1). Once in the overlay control table, a fine tune $F_n$ may be determined from the first series of measurements 108 by, e.g., subtracting each of the first series of measurements 108 from an average process offset K (which may be zero for initial measurements). Such a process is described further in U.S. Pat. No. 7,031,794, the contents of which are hereby incorporated herein by reference.

In an embodiment the SOC process may generate an inter-field model as well as an intra-field model. In a particular embodiment the inter-field model may use the following equations:

$$d_X = T_X - (R_W + N) \cdot Y + S_X \cdot X$$

$$d_Y = T_Y + R_W \cdot X + S_Y \cdot Y$$

Where: $d_x$=inter-field x direction overlay errors
$d_y$=inter-field y direction overlay errors
$T_x$=inter-field x direction translations
$T_y$=inter-field y direction translations
$R_w$=wafer rotation
N=non-orthogonality
$S_x$=x direction wafer scaling coefficients
X=x direction in the inter-field coordinate system, with respect to the center of wafer
$S_y$=y direction wafer scaling coefficients
Y=y direction in the inter-field coordinate system, with respect to the center of wafer Additionally in this embodiment the SOC process may also generate an intra-field model, which may use the following equations:

$$d_x = T_x - (R_S + R_A) \cdot y + (M_S + M_A) \cdot x$$

$$d_y = T_y + (R_S - R_A) \cdot x + (M_S - M_A) \cdot y$$

Where: $R_S$=symmetrical field rotation
$R_A$=asymmetrical field rotation
$M_S$=symmetrical field magnification
$M_A$=asymmetrical field magnification
y=y direction in the intra-field coordinate system, with respect to the center of a field
x=x direction in the intra-field coordinate system, with respect to the center of a field
Tx=intra-field x direction translations
Ty=intra-field y direction translations However, while one first order process (e.g., the SOC process) is described above, this description is intended to be illustrative and is not intended to be limiting upon the embodiments. Rather, any suitable first order process, such as y=ax+b, may alternatively be utilized. All such processes are fully intended to be included within the scope of the embodiments.

However, instead of performing only a single order correction on the first series of measurements 108, the model creation engine 107 additionally performs higher order corrections, such as second order corrections, third order corrections, fourth order corrections, or higher order corrections. In one embodiment the model creation engine 107 performs a third order correction such as an intra-field high order parameter correction (iHOPC). In an embodiment the iHOPC correction may be performed using the following equations (which may incorporate the equations from the single order correction discussed above):

$$d_x{}^i = T_x{}^i + (M_S{}^i + M_A{}^i) \cdot x - (R_S{}^i + R_A{}^i) \cdot y + K_7{}^i x^2 + K_{11}{}^i y^2 + K_{13}{}^i x^3 + K_{19}{}^i y^3$$

$$d_y{}^i = T_y{}^i + (M_S{}^i - M_A{}^i) \cdot x + (R_S{}^i - R_A{}^i) \cdot x + K_8{}^i y^2 + K_{10}{}^i yx + K_{12}{}^i x^2 + K_{14}{}^i y^3 + K_{16}{}^i y^2 x$$

Wherein: $d^i{}_x$=the sum of the inter-field and intra-field x direction overlay errors in the ith field
$d^i{}_y$=the sum of the inter-field and intra-field y direction overlay errors in the ith field
$T^i{}_x$=intra-field x direction translations in the ith field
$T^i{}_y$=intra-field y direction translations in the ith field
$M^i{}_S$=symmetrical field magnification in the ith field
$M^i{}_A$=asymmetrical field magnification in the ith field
x=x direction in the intra-field coordinate system, with respect to the center of a field
$R^i{}_S$=symmetrical field rotation in the ith field
$R^i{}_A$=asymmetrical field rotation in the ith field
y=y direction in the intra-field coordinate system, with respect to the center of a field
$K^i{}_7$=x direction $2^{nd}$ order magnification in the ith field
$K^i{}_{11}$=y direction bow in the ith field
$K^i{}_{13}$=x direction $3^{rd}$ order magnification in the ith field
$K^i{}_{19}$=y direction $3^{rd}$ order flow in the ith field
$K^i{}_8$=$2^{nd}$ magnification in the ith field
$K^i{}_{10}$=trapezoid in the ith field
$K^i{}_{12}$=x direction bow in the ith field
$K^i{}_{14}$=y direction $3^{rd}$ order magnification in the ith field
$K^i{}_{16}$=accordion in the ith field Once the single order correction (e.g., the SOC correction) and the third order correction have been performed, the single order correction and the third order correction may be used to generate a pseudo full sample of the first semiconductor wafer 102, wherein each of the semiconductor dies 205 has a full sample of 12 data points, some of which are the actual measurements (as described above) and the rest being generated from the first order correction and the third order correction. In other words, by using the uniform scattered methodology 105 to obtain the first series of measurements 108, and then using the first order correction and the third order correction to generate the a representative full sample of twelve measurements for each semiconductor die 205, a full set of representative data may be generated for the following higher order correction (as described further below).

In an embodiment the pseudo full sample may be created using a Taylor series to fill up any missing values. For example, in one embodiment which uses the Taylor series to fill up the missing values, the following equations may be utilized:

$$dx = a1 + a2x + a3y + a4x^2 + a5xy + a6y^2 + a7x^3 +$$

$$dy = b1 + b2x + b3y + b4x^2 + b5xy + b6y^2 + b7x^3 +$$

Where: dx=x direction overlay errors
dy=y direction overlay errors
a1~a7=Taylor coefficients
b1~b7=Taylor coefficients Once the pseudo samples have been generated from the single order correction and the third order correction, the model creation engine 107 may perform another higher order correction using the pseudo sample. In an embodiment the model creation engine 107 may perform a higher order inter field process correction such as a correction per exposure (CPE) correction in order to generate the final overlay measurement data 109. In an embodiment the CPE correction may be performed using the following equations:

$$d_x = T_x - (R_S + R_A) \cdot y + (M_S + M_A) \cdot x$$

$$d_y = T_y + (R_S - R_A) \cdot x + (M_S - M_A) \cdot y$$

Where $d_x$, $d_y$, $T_x$, $T_y$, $R_S$, $R_A$, y, $M_s$, $M_A$, and x are as described above.

Once the model creation engine 107 has generated the various models in the form of overlay measuring data 109 using the first order correction (e.g., the SOC) as well as the higher order corrections (e.g., the iHOPC and the CPE), the overlay measurement data 109 may be stored until such a time as it is ready to be used. In an embodiment the overlay measuring data 109 may be stored in a database 111 that is connected to the exposure tool 101 through, e.g., an automatic data transmission interface 115. Alternatively, the database 111 may be disconnected from the exposure tool 101, or connected during times of data transfer. Any suitable method of storage may alternatively be utilized.

In an embodiment the database 111 may store additional information in addition to the overlay measuring data 109. For example, the database 111 may also store a mask database 112 and an overlay offset database 114. The mask database 112 may provide information on the various features and exposure parameters of the patterned masks utilized by the exposure tool 101 in, for example, a design standard such as OASIS, DDSII, or MEBES®, a registered trademark of Applied Materials. The overlay offset database 114 includes overlay offsets that have been previously generated (e.g., designed for each mask or designed for the exposure tool 101 itself) that may be applied to patterned masks within the mask database 112 in order to correct for overlay offset issues that are already known prior to the exposure of the first semiconductor wafer 102.

Once the overlay measuring data 109 is ready, the overlay measuring data 109 may be utilized in a step of predicting the overlay error correction 113 that will minimize the overlay error for the exposure of the second semiconductor wafer 104. In an embodiment the overlay error correction may be predicted using an algorithm to apply the overlay measuring data 109 (generated by, e.g., the SOC, iHOPC and CPE corrections) to data within the overlay offset database 114 in order to generate a first updated set of overlay error correction.

Once the first updated set of overlay error correction has been generated, the first updated set of overlay error correction may be sent at the appropriate time to the exposure tool 101 using, e.g., the automatic data transmission interface 115. In an embodiment the automatic data transmission interface 115 is a wired link to, e.g., the exposure tool 101 that allows data from the database 111 (such as the data related to the patterned masks within the mask database 112 and the first updated set of overlay error correction) to be sent to the exposure tool 101 either automatically, upon a command from the exposure tool 101, or else through a manual input by a user. Alternatively, the automatic data transmission interface 115 may be a wired link to a local area network (LAN) or a wide area network (WAN) and/or a wireless link. Any suitable method and device for transferring the data from the database 111 to the exposure tool 101 may alternatively be utilized.

Once the data from the database 111 has been received at the exposure tool 101, the exposure tool 101 utilizes the data to set the various exposure process parameters based upon the data received. In particular, the data related to the patterned mask from the mask database 112 may provide an initial set of exposure process parameters to be utilized with a particular patterned mask, and then the initial exposure process parameters may be modified by applying the updated set of overlay error correction to the initial exposure process parameters.

Once the exposure tool has had the various exposure process parameters modified in order to at least partially correct the overlay errors that were measured in the preceding run (with, e.g., the exposure of the first semiconductor wafer 102), the second semiconductor wafer 104 is placed into the exposure tool 101 and a second photoresist (not separately illustrated) is exposed using the updated set of overlay error correction.

Once the second semiconductor wafer 104 has been exposed, the second semiconductor wafer 104 will also follow a similar path of measurements described above with respect to the first semiconductor wafer 102. For example, the second semiconductor wafer 104 is measured using the uniform scattered methodology 105 to obtain a second series of measurements, such as by initially being separated into different regions ($R_1, R_2, R_3, \ldots$) and a single measurement (chosen randomly) is taken from each of the semiconductor dies 205 within the second semiconductor wafer 104. Additionally, a center region $R_c$ of the second semiconductor wafer 104 is identified and a separate set of measurements are taken of the semiconductor dies within the central region $R_c$ of the second semiconductor wafer 104.

Once the second series of measurements have been taken, THE second series of measurements are fed into the model creation engine 107, and overlay measuring data 109 from the second semiconductor wafer 104 is generated (using, e.g., the SOC, iHOPC and CPE corrections as described above) and stored in the database 111. Once stored, the overlay measuring data 109 from the second semiconductor wafer 104 is applied to the first updated set of overlay error correction (generated from the overlay measuring data 109 from the first semiconductor wafer 102) in order to generate a second updated set of overlay error correction. This second updated set of overlay error correction is then forwarded to the exposure tool 101 through the automatic data transmission interface 115 and used to prepare the exposure tool 101 for a third semiconductor wafer 106.

Figure 6:
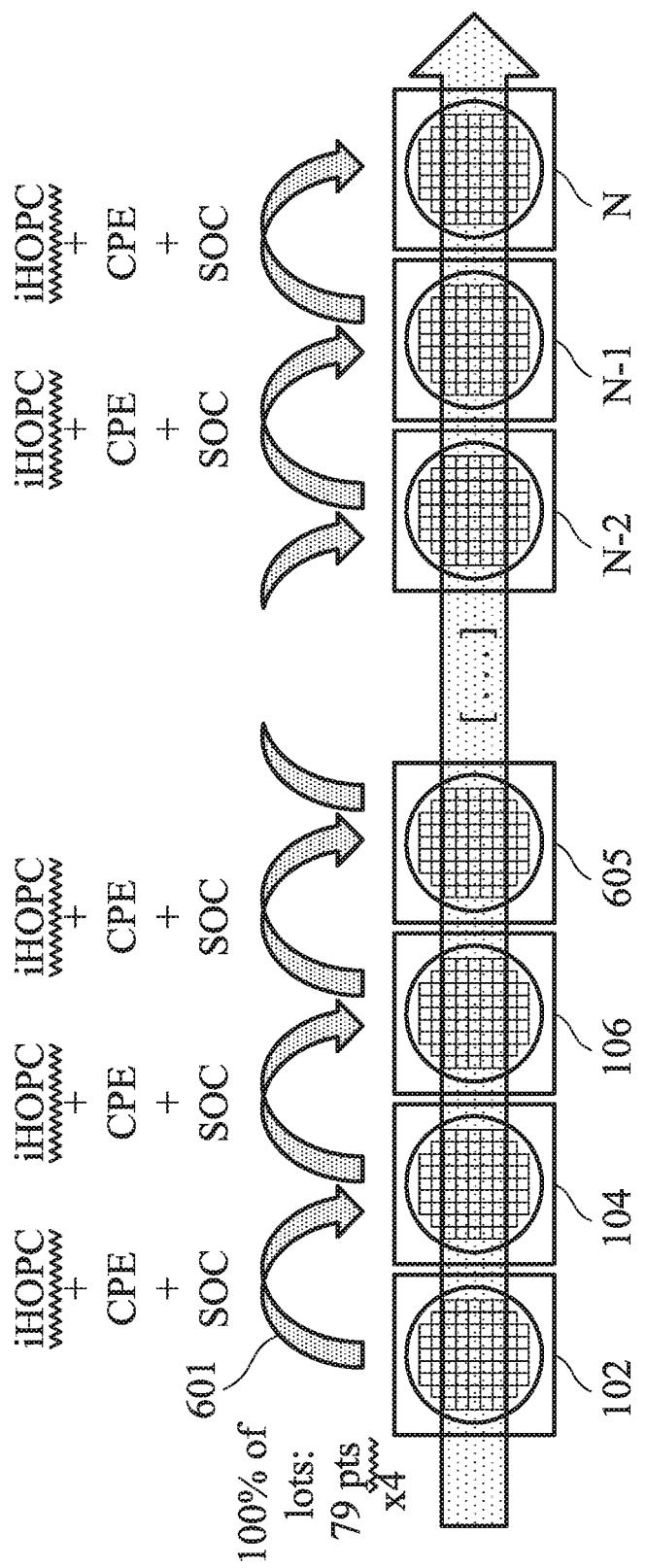
FIG. 6 illustrates a run-to-run measurement process according to one or more embodiments of the present disclosure.

FIG. 6 illustrates the sequential nature of the above described process as it is applied to multiple semiconductor wafers that are exposed using the exposure tool 101. In FIG. 6, there are shown the first semiconductor wafer 102 which has been measured and the first order correction (e.g., SOC), the higher order intra-field error correction (e.g., the iHOPC), and the higher order inter-field error correction (e.g., CPE) are utilized to determine the error correction that will be utilized for the second semiconductor wafer 104. The use of the error correction determined by a previous semiconductor wafer on a next subsequent semiconductor wafer is represented in FIG. 6 by the arrow labeled 601.

This process is repeated as illustrated by using the error correction determined from the second semiconductor wafer 104 to modify the exposure parameters for the third semiconductor wafer 106, and the measurements of the third semiconductor wafer 106 are used to modify the exposure parameters for a fourth semiconductor wafer 605 and so on. The process may be continued, with each previous semiconductor wafer providing the correction data used to correct the exposure parameters for the next semiconductor wafer as long as desired, such as N number of semiconductor wafers.

However, for each exposure run of a single semiconductor wafer, each of the first order correction (e.g., SOC), the higher order intra-field error correction (e.g., the iHOPC), and the higher order inter-field error correction (e.g., CPE) are utilized on each semiconductor wafer for a 100% measurement of semiconductor wafers. However, by using the uniform scattering methodology described above, a reduced number of measurements are taken (e.g., 1 per semiconductor die and 1 per semiconductor die within the central region $R_c$).

In a particular example, in an embodiment in which seventy die are to be manufactured per semiconductor wafer, a total of seventy measurements are taken, with one measurement per semiconductor die manufactured on the semiconductor wafer. Additionally, in an embodiment in which there are nine semiconductor dies 205 within the central region $R_c$, a total of nine measurements are taken from the central region $R_c$. As such, there are a total of 79 measurements taken per each semiconductor wafer, or 316 measurements for a run of four semiconductor wafers, or 3,160 measurements for ten runs of four semiconductor wafers per run.

Previous methods, which performed measurements on seventeen inter-field locations and twelve intra-field measurements at each location (for a total of two hundred and four measurements for each semiconductor wafer), and then, for only ten percent of the lots exposed perform nine hundred and twenty-one measurements for the higher order analyses, there are a total of 10,002 measurements taken in ten runs of four semiconductor wafers per run. However, by using the combined sampling and performing the first order correction as well as the higher-order corrections for each run of semiconductor wafers as described above, fewer measurements are taken per semiconductor wafer while still achieving an improvement in overlay control.

For example, using the numbers above, for ten lots of four semiconductor wafers the process described above with respect to FIGS. 1-6 will utilize 3,160 measurements (79 measurements per semiconductor wafer*4 wafers per lot*10 lots). Similarly, using previous processes which utilize 204 measurements per semiconductor wafer as well as 921 measurements for the higher order corrections for 2 of the semiconductor wafers per 10 lots, there are 10,002 measurements used ((204 measurements per semiconductor wafer*4 wafers per lot*10 lots+921 measurements per wafer*2 semiconductor wafers). As such, there is a reduction of over 6,842 measurements with comparable results. In particular, test results indicate that raw data overlay errors using 10,002 measurements are 4.1/4.8 (in an X/Y nm format) while using the uniform scattered methodology with only 3,160 measurements has raw data overlay errors of 3.5/4.7. Additionally, residual data using 10,002 measurements are 3.7/3.0 while the residual data using the uniform scattered methodology is 2.6/2.9.

In another example, by utilizing the process described above with respect to FIGS. 1-6, the raw data improvement can be increased by 1.2 nm (from 3.9 to 2.7) in, e.g., an X direction and increased by 0.6 nm (from 3.5 to 2.9) in, e.g., a Y direction over a process that utilizes a 100% sampling for a first order correction and higher order corrections (e.g., iHOPC and CPE) on 10% of the semiconductor wafers in a lot of 10 semiconductor wafers. This occurs with a sampling reduction of about 70%, from 10,362 samples to 3160, which results in significant cost savings.

Figures 7A, 7B:
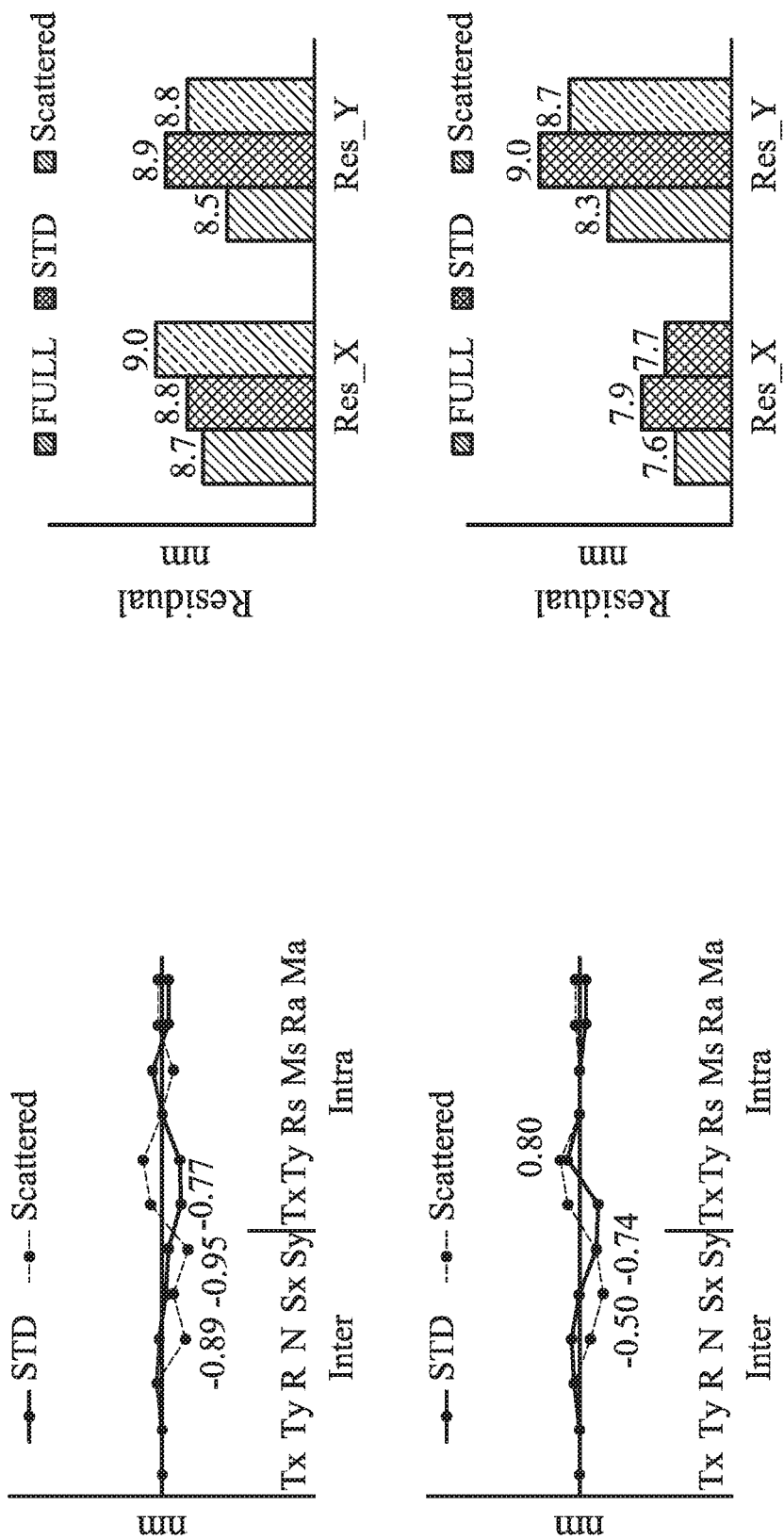
FIGS. 7A-7B illustrate test data that of an embodiment of the present disclosure.

FIGS. 7A-7B illustrate these comparable results in another fashion. The charts in FIGS. 7A-7B illustrate test results of the uniform scattered methodology (on a semiconductor wafer with 64 fields) as described above compared to a process which utilizes thirteen fields and eight measurements per field (for a total of 104 points per semiconductor wafer). As can be seen, at two separate points in the manufacturing process (e.g., two different layers), the uniform scattered methodology has comparable model error (illustrated in FIG. 7A) and residual performance (illustrated in FIG. 7B). However, there is an approximate 38% reduction in the number of sampling points utilized from 104 points per wafer to 64 points per wafer.

Figure 8:
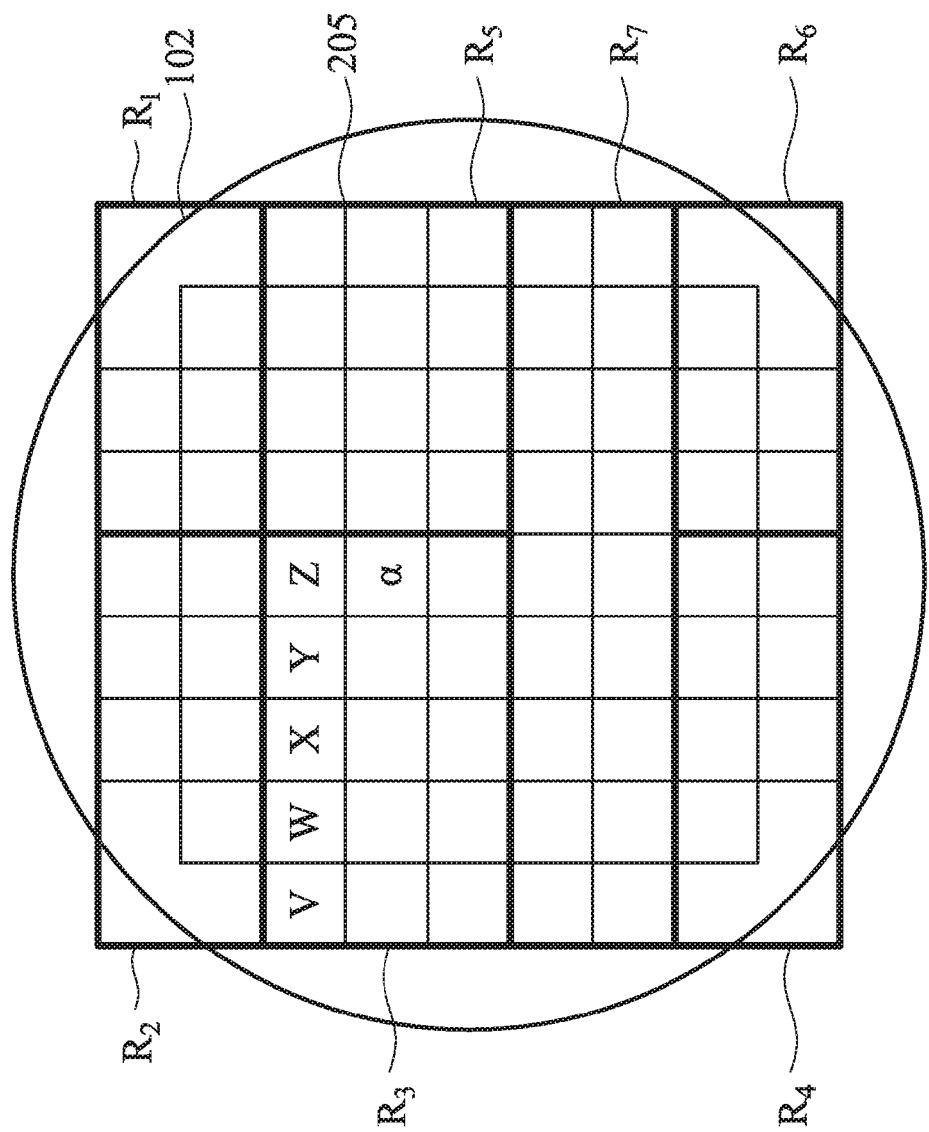
FIG. 8 illustrates a second division of the semiconductor wafer into separate regions according to an embodiment of the present disclosure.

FIG. 8 illustrates another embodiment in which the semiconductor wafer 102 is divided into a total of seven regions. In this embodiment the first region $R_1$, the second region $R_2$, the third region $R_3$, the fourth region $R_4$, the fifth region $R_5$, and the sixth region $R_6$ are joined by a seventh region $R_7$. In this embodiment the different regions may be separated as desired, and illustrates that the semiconductor wafer 102 may be divided into any suitable number of regions with any suitable number of semiconductor dies 205 (e.g., semiconductor dies 205 labeled "V"-"Z") per individual region. Such divisions may be based on field size, although other divisions may also be utilized. For example, if some fields have a strong correlation and will have similar error overlays, but are not in adjoining regions these fields may still be divided into the same region. Alternatively, if the semiconductor wafer 102 is desired to be separated into equal parts, then a full cluster region division may be utilized. Any suitable separation of the semiconductor wafer 102 may alternatively be utilized, and all such separations are fully intended to be included within the scope of the embodiments.

According to an aspect of this description, a method of manufacturing a semiconductor device comprising exposing a first semiconductor wafer and performing a first series of measurements on the first semiconductor wafer to obtain a first set of overlay offset measurements is provided. The first set of overlay offset measurements are utilized to generate a first overlay offset model based off of a first order correction, an intra-field higher order correction, and as inter-field higher order correction. A first set of overlay offsets is generated from the first overlay offset model. A second semiconductor wafer is exposed based at least in part on the first set of overlay offset, wherein the second semiconductor wafer is exposed directly after the exposing the first semiconductor wafer. A second series of measurements is performed on the second semiconductor wafer to obtain a second set of overlay offset measurements, and the second set of overlay offset measurements is utilized to generate a second overlay offset model based off of the first order correction, the intra-field higher order correction, and the inter-field higher order correction.

According to another aspect of this description, a method of manufacturing a semiconductor device comprising taking a first set of overlay offset measurements of a first semiconductor wafer is provided. A plurality of correction analyses is performed on the first set of overlay offset measurements to generate a first overlay offset model, wherein the plurality of correction analyses further comprises a first order correction, a first intra-field higher order correction, and a first inter-field higher order correction. The overlay offset model is utilized to expose a second semiconductor wafer, wherein the second semiconductor wafer is the next semiconductor wafer to be exposed after the first semiconductor wafer. A second set of overlay offset measurements of the second semiconductor wafer is taken, and the plurality of correction analyses are performed on the second set of overlay offset measurements to generate a second overlay offset model.

According to yet another aspect of this description, a overlay correction unit comprising a measurement unit is provided. The measurement unit is configured to perform run-to-run measurements on each of a plurality of semiconductor wafers. A model generation unit is configured to generate a plurality of models using a series of correction techniques, each of the plurality of models being generated from a corresponding one of the plurality of semiconductor wafers, wherein the series of correction techniques comprises a first order correction a first intra-field higher order parameter correction and a first inter-field higher order parameter correction.

In the preceding detailed description, various embodiments have been described. It will, however, be apparent to a person of ordinary skill in the art that various modifications, structures, processes, and changes may be made thereto without departing from the broader spirit and scope of the present disclosure. The specification and drawings are, accordingly, to be regarded as illustrative and not restrictive. It is understood that embodiments of the present disclosure are capable of using various other combinations and environments and are capable of changes or modifications within the scope of the claims and their range of equivalents.

What is claimed is:

1. A method of manufacturing a semiconductor device, the method comprising:
   exposing a first semiconductor wafer;
   performing a first series of measurements on the first semiconductor wafer to obtain a first set of overlay offset measurements;
   utilizing the first set of overlay offset measurements to generate a first overlay offset model based off of a first order correction, an intra-field higher order correction, and as inter-field higher order correction;
   generating a first set of overlay offsets from the first overlay offset model;
   exposing a second semiconductor wafer based at least in part on the first set of overlay offset, wherein the second semiconductor wafer is exposed directly after the exposing the first semiconductor wafer;
   performing a second series of measurements on the second semiconductor wafer to obtain a second set of overlay offset measurements; and
   utilizing the second set of overlay offset measurements to generate a second overlay offset model based off of the first order correction, the intra-field higher order correction, and the inter-field higher order correction.

2. The method of claim 1, wherein the first order correction comprises a smart overlay control.

3. The method of claim 2, wherein the intra-field higher order correction comprises an intra-field high order parameter correction.

4. The method of claim 3, wherein the inter-field higher order correction comprises a correction per exposure.

5. The method of claim 1, wherein the performing the first series of measurement comprises:
   taking a first set of measurements, wherein the first set of measurements comprises a single measurement from each semiconductor device of the first semiconductor wafer; and
   taking a second set of measurements separately from the first set of measurements, wherein the second set of measurements comprises a single measurement from each semiconductor device within a central region of the first semiconductor wafer.

6. The method of claim 5, wherein the taking the single measurement from each field further comprises separating the first semiconductor wafer into a plurality of regions.

7. The method of claim 1, further comprising storing the first overlay offset model in a database.

8. A method of manufacturing a semiconductor device, the method comprising:
   taking a first set of overlay offset measurements of a first semiconductor wafer;
   performing a plurality of correction analyses on the first set of overlay offset measurements to generate a first overlay offset model, wherein the plurality of correction analyses further comprises:
   a first order correction;
   a first intra-field higher order correction; and
   a first inter-field higher order correction;
   utilizing the overlay offset model to expose a second semiconductor wafer, wherein the second semiconductor wafer is the next semiconductor wafer to be exposed after the first semiconductor wafer;
   taking a second set of overlay offset measurements of the second semiconductor wafer; and
   performing the plurality of correction analyses on the second set of overlay offset measurements to generate a second overlay offset model.

9. The method of claim 8, further comprising:
   utilizing the second overlay offset model to expose a third semiconductor wafer, wherein the third semiconductor wafer is the next semiconductor wafer to be exposed after the second semiconductor wafer;
   taking a third set of overlay offset measurements of the third semiconductor wafer; and
   performing the plurality of correction analyses on the third set of overlay offset measurements.

10. The method of claim 8, wherein the taking the first set of overlay offset measurements further comprises:
    taking at least one first measurement from each semiconductor device on the semiconductor wafer: and
    taking at least one second measurement from each semiconductor device within a central region of the semiconductor wafer, wherein the at least one second measurement from each semiconductor device within the central region are different than the at least one first measurement from each semiconductor device.

11. The method of claim 8, wherein the first order correction comprises a smart overlay control.

12. The method of claim 11, wherein the intra-field higher order correction comprises an intra-field high order parameter correction.

13. The method of claim 12, wherein the inter-field higher order correction comprises a correction per exposure.

14. The method of claim 8, wherein the utilizing the overlay offset model to expose a second semiconductor wafer is performed to expose a photosensitive material on the second semiconductor wafer.

15. A method of manufacturing a semiconductor device, the method comprising:
    performing run-to-run measurements on each of a plurality of semiconductor wafers with a measurement unit; and
    generating a plurality of models using a series of correction techniques with a model generation unit, each of the plurality of models being generated from a corresponding one of the plurality of semiconductor wafers, wherein the series of correction techniques comprises:
    a first order correction;
    a first intra-field higher order parameter correction; and
    a first inter-field higher order parameter correction.

16. The method of claim 15, further comprising storing the plurality of models in a database.

17. The method of claim 15, wherein the first order correction is a smart overlay control.

18. The method of claim 17, wherein the first intra-field higher order parameter correction comprises intra-field high order parameter correction.

19. The method of claim 18, wherein the first inter-field higher order parameter correction comprises a correction per exposure.

20. The method of claim 15, further comprising performing imaging upon each one of the plurality of semiconductor wafers using a camera.

* * * * *